United States Patent [19]
Yamaguchi et al.

[11] Patent Number: 4,822,789
[45] Date of Patent: Apr. 18, 1989

[54] METHOD OF PRODUCING RENAL FUNCTION-IMPROVING EFFECT AND DIURETIC EFFECT ON WARM-BLOODED ANIMAL

[75] Inventors: Isao Yamaguchi, Tokyo; Yoshiaki Akimoto, Kawaguchi; Taku Nagao, Tokyo, all of Japan

[73] Assignee: Tanabe Seiyaku Co., Ltd., Japan

[21] Appl. No.: 150,619

[22] Filed: Feb. 1, 1988

[30] Foreign Application Priority Data
Feb. 10, 1987 [JP] Japan .................................. 62-29396

[51] Int. Cl.$^4$ ............................................. A61K 31/55
[52] U.S. Cl. .................................................... 514/211
[58] Field of Search ......................................... 514/211

[56] References Cited
U.S. PATENT DOCUMENTS
3,562,257  2/1971  Kugita et al. ........................ 514/929
4,567,175  11/1986  Takeda et al. ....................... 514/211

FOREIGN PATENT DOCUMENTS
2154577  9/1985  United Kingdom ................ 514/211
2154578  9/1985  United Kingdom ................ 514/211

Primary Examiner—Allen J. Robinson
Attorney, Agent, or Firm—Scully, Scott, Murphy & Presser

[57] ABSTRACT

Disclosed is a method for producing a renal function-improving and diuretic effects on a warm-blooded animal which comprises administering to the warm-blooded animal a therapeutically effective amount of 2-(4-methoxyphenyl)-3-acetoxy-5-[2-(dimethylamino)ethyl]-8-chloro-2,3-dihydro-1,5-benzothiazepin-4(5H)-one or a pharmaceutically acceptable acid addition salt thereof.

7 Claims, No Drawings

METHOD OF PRODUCING RENAL FUNCTION-IMPROVING EFFECT AND DIURETIC EFFECT ON WARM-BLOODED ANIMAL

BACKGROUND OF THE INVENTION

The present invention relates to a method of producing a renal function-improving effect and a diuretic effect on a warm-blooded animal.

It has been known that 2-(4-methoxyphenyl)-3-acetoxy-5-[2-(dimethylamino)ethyl]-8-chloro-2,3-dihydro-1,5-benzothiazepin-4(5H)-one or a pharmaceutically acceptable acid addition salt thereof has excellent hypotensive activity and cerebral or coronary vasodilating activity (Japanese Unexamined Patent Publication No. 225174/1984).

SUMMARY OF THE INVENTION

The present invention provides a method of producing a renal function-improving effect and a diuretic effect on a warm-blooded animal which comprises administering to said warm-blooded animal a therapeutically effective amount of 2-(4-methoxy-phenyl)-3-acetoxy-5-[2-(dimethylamino)ethyl]-8-chloro-2,3-dihydro-1,5-benzothiazepin-4(5H)-one (hereinafter abbreviated as 8-chlorobenzothiazepine compound) or a pharmaceutically acceptable acid addition salt thereof.

DESCRIPTION OF THE PREFERRED EMBODIMENTS

The above 8-chloro-benzothiazepine compound which is an active ingredient of the present invention has excellent renal function-improving activity and diuretic activity.

For example, in case where the 30 minutes clamping is applied to the renal artery in the rats after contralateral nephrectomy, they will suffer from an ischemia-induced acute renal failure. Moreover, when glycerol is intramuscularly administered to rats, they will suffer from acute renal failure. In these cases, values of urea nitrogen and creatinine in blood of the rats will be abnormally increased as in the case of human acute renal failure. The 8-chloro-benzothiazepine compound which is the active ingredient of the present invention exhibits an excellent effect that these values are excellently improved. Also, when a stroke-prone spontaneously hypertensive rat (SHRSP) is fed with a diet containing sodium chloride, renal disorder (azotemia) which is similar to chronic renal failure will be caused and kidney lesions (e.g. atrophy of uriniferous tubules, collapse or sclerosis of glomerular tufts) may be observed. However, in cases where the 8-chlorobenzothiazepine compound which is the active ingredient of the present invention is administered, the compound exhibits an excellent effect that such lesions in kidney can be prevented. Accordingly, the pharmaceutical preparation of the present invention having such effects can be used for prophylactic and therapeutic agents for renal failure.

Further, when the above 8-chloro-benzothiazepine compound which is the active ingredient of the present invention is orally administered to SHR (dose: 10 mg/kg), the compound exhibits an excellent effect such that urine volume and amount of sodium ion and chloride ion excreted in the urine are increased by 70% or more, respectively, without affecting the excretion of potassium. Therefore, the pharmaceutical preparation of the present invention can be used for a diuretic agent which has no fear of causing hypokalemia.

The agent having a renal function-improving effect and a diuretic effect of the present invention can be used by both oral and parenteral administration to a warm-blooded animal including a human being. When used orally, the 8-chloro-benzothiazephine compound or a pharmaceutically acceptable acid addition salt thereof can be used as such or in the form of pharmaceutical preparations suitable for oral administration with pharmaceutically acceptable carriers such as excipients, binding agents, disintegrators and lubricants. The pharmaceutically acceptable carriers include, for example, starch, lactose, glucose, gelatin, sorbit, tragacanth, polyvinyl pyrrolidone, sugar, corn starch, polyethylene glycol, talc, potassium phosphate, magnesium stearate and other conventional excipients, binding agents, disintegrators and lubricants. The preparation for administration may be in solid form such as tablets, capsules, granules, microcapsules and suppositories, or in liquid form such as solutions, suspensions and emulsions. For parenteral administration, the agent of the present invention may be suitably used in the form of injections. For the solvent for the injections, distilled water for injection, vegetable oil and propylene glycol can be used. Further, the injection may contain solubilizers, buffers and stabilizers.

The 8-chloro-benzothiazepine compound, which is an active ingredient of the present invention, can be used in the form of free base or a pharmaceutically acceptable acid addition salt thereof. The pharmaceutically acceptable acid addition salt can be, for example, inorganic acid salts such as hydrochloride, hydrobromide, hydroiodide, perchlorate, sulfate and phosphate, or organic acid salts such as oxalate, maleate, fumarate, tartrate and methanesulfonate.

The dose of the agent of the present invention may vary depending on the disease condition, the age, body weight and severity of symptoms of the patient, administration route, etc., but the proper dose of the 8-chlorobenzothiazepine compound or a pharmaceutically acceptable acid addition salt thereof may be in the range of 0.05 to 100 mg/day/kg, preferably in the range of 0.1 to 30 mg/day/kg.

As mentioned above, since the agent of the present invention has an effect for improving the abnormality in concentrations of urea nitrogen and creatinine in blood under the state of renal failure, as well as it prevents the kidney lesions in the chronic renal failure, the agent can be used for the treatment and prophylaxis for acute and chronic renal failures resulting from various renal diseases such as glomerulonephritis, nephrotic syndrome, nephrosclerosis, tubular disorder and ischemic renal failure.

Further, since the agent of the present invention acts for increasing urine volume and amounts of sodium ion and chloride ion in the urine without affecting the excretion of potassium, it can be used for the treatment of symptoms of edema, renal failure, etc. as a diuretic agent which has no fear of causing hypokalemia.

Since the 8-chloro-benzothiazepine compound which is the active ingredient of the present invention has two asymmetric carbon atoms in the molecule, there exist two kinds of stereoisomers (namely, cis- and trans-isomers) or four kinds of optical isomers (namely, (+)-cis-, (−)-cis-, (+)-trans- and (−)-trans-isomers). For the object of the present invention, any of these isomers and mixtures thereof can be used, but in general it is preferable to use a cis-isomer.

EXPERIMENTAL EXAMPLE 1

(Effect on ischemic acute renal failure)

(+)-Cis-2-(4-methoxyphenyl)-3-acetoxy-5-[2-(dimethylamino)ethyl]-8-chloro-2,3-dihydro-1,5-benzothiazepin-4(5H)-one maleate was used as the test compound.

Ischemic acute renal failure (ARF) was induced in male Sprague-Dauley rats (one group consisting of 11 rats) weighing 270 to 360 g. They were fasted overnight and anesthetized with pentobarbital Na (50 mg/kg i.p.). After right nephrectomy, the left renal artery was clamped for 30 minutes. An intravenous infusion of saline or the test compound solution was started in all animals 15 minutes before the initiation of clamping and was continued during the 30-minutes clamping period. The abdominal wall was closed and the rats were placed in individual cages. Urine was collected for 24 hours under free access to food and water. 24 Hours later, blood was drawn for analysis.

Three groups of rats studied were as follows:
(1) Sham operated rats (sham)
(2) Untreated control animals with ischemic ARF. (ARF control)
(3) Ischemic ARF, treated by the intravenous infusion of the test compound at a rate of 20 μg/kg/min.

Plasma urea and creatinine, and urine creatinine, sodium, osmolarity and NAG (N-acetyl-β-D-Glucosaminidase) were determined by standard methods. Creatinine clearance, fractional excretion of sodium and NAG index were calculated with standard formulas.

(Results)

The results are shown in Table 1.

TABLE 1

| Dose μg/kg/min. | PUN (mg/dl) | Pcr (mg/dl) | FENa (%) | Ccr (ml/24 hr) | Uosm (mOsm/kg) $H_2O$ | NAG-index Unit of creatinine |
|---|---|---|---|---|---|---|
| Sham | 23.2 ± 1.7 | 0.7 ± 0.04 | 0.54 ± 0.10 | 1589 ± 123 | 1286 ± 123 | 33.8 ± 5.6 |
| ARF Control | 101.9## ± 8.6 | 3.3## ± 0.4 | 9.67## ± 2.34 | 236## ± 78 | 598## ± 43 | 83.5## ± 7.5 |
| 20 | 63.7## ± 10.0* | 1.7 ± 0.3* | 2.90 ± 1.25 | 816## ± 170** | 818## ± 74 | 66.6# ± 12.0 |

P 0.05,
P < 0.01 vs Sham Group
*P < 0.05,
**P < 0.01 vs AF Control Group
PUN; Plasma Urea Nitrogen Concentration
Pcr; Plasma Creatinine Concentration
FENa; Fractional Excretion of Sodium
Ccr; Creatinine Clearance
Uosm; Urine Osmolarity
NAGindex; N—Acetyl-β-D-Glucosaminidase index As can be seen from Table 1, twenty-four hours after the ischemic insult, the untreated control rats caused marked increases in plasma urea (PUN) and creatinine (Pcr) levels and a significant decrease in creatinine clearance (Ccr) value. These rats also had higher fractional excretion of sodium (FENa) and NAG index, and lower urinary osmolarity (Uosm). Thus, the untreated control rats showed an acute renal failure (ARF).

ARF rats treated with the test compound (20 μg/kg/min) exhibited significantly lower PUN, Pcr, FENa and NAG index, and higher Ccr than those in the untreated control rats.

This means that the test compound is effective in reducing the severity of ischemic acute renal failure.

EXPERIMENTAL EXAMPLE 2

(Effect on Glycerol-Induced Acute Renal Failure in Rats)

SD strain male rats (age: 7 weeks; one group consisting of 4 to 5 rats) dehydrated for 24 hours were administered intramuscularly at femoral region with 50% glycerolphysiological saline at a dose of 10 ml/kg.

In order to examine the effect of the present pharmaceutical preparation on the acute renal failure induced under such experimental conditions, the test compound administration groups had been orally administerd with an aqueous solution of (+)-cis-2-(4-methoxyphenyl)-3-acetoxy-5-[2-(dimethylamino)ethyl]-8-chloro-2,3-dihydro-1,5-benzothiazepin-4(5H)-one maleate at a dose of 10 mg/kg and 30 mg/kg, respectively, at a prescribed time of the day for the three days before the administration of glycerol. After administration of the glycerol, the test compound was orally administered in the similar manner.

On the other hand, the control group was orally administered with water instead of the test compound solution.

After three days of the administration of the glycerol, celiotomy was conducted for each rat of the both groups under ether anesthesia, and blood was collected from the abdominal aorta. Then, serum separated from said blood was subjected to a biochemical analysis.

(Result)

Results are shown in Table 2 below.

TABLE 2

| | Test compound administration group (dose: mg/kg/day) | | Control group |
|---|---|---|---|
| | 10 | 30 | — |
| Serum urea nitrogen (mg/dl) | 81.3 ± 39.4 | 66.4 ± 13.1 | 119.1 ± 89.3 |
| Serum creatinine (mg/dl) | 1.68 ± 0.68 | 1.28 ± 0.14 | 3.37 ± 1.41 |

From the above Table, it can be recognized that the concentrations of serum urea nitrogen and creatinine are remarkably increased in the control group with acute renal failure. However, in the test compound administration group, the concentrations are lowered dose-dependently in both cases, and therefore it is apparent that the onset of acute renal failure are inhibited.

EXPERIMENTAL EXAMPLE 3

(Effect on Chronic Renal Failure in Rats)

Stroke-prone spontaneously hypertensive rats (SHRSP, age: 13 weeks, one group consisting of 8 rats) were fed with a powder diet containing 8% sodium chloride for three weeks. In order to examine the effect of the pharmaceutical preparation of the present invention on chronic renal failure induced under such conditions, the test compound administration group was fed with a powder diet containing 8% sodium chloride and 1000 ppm of (+)-cis-2-(4-methoxyphenyl)-3-acetoxy-5-[2-(dimethylamino)ethyl]-8-chloro-2,3-dihydro-1,5-benzothiazepin-4(5H)-one maleate for three weeks. On the other hand, the control group was fed with a powder diet containing 8% sodium chloride for 3 weeks.

After the feeding, celiotomy was conducted for each rat under ether anesthesia, and blood was collected from the abodominal aorta and then the rats were killed. The collected blood was subjected to a biochemical analysis, as well as the kidney was subjected to a histopathological examination.

(Result)

Results are shown in Table 3 below.

TABLE 3

|  | Test compound administration group | Control group |
|---|---|---|
| Atrophy of uniniferous tubule | Δ 0/8<br>▲ 0/8 | Δ 2/8<br>▲ 5/8 |
| Collapse or sclerosis of glomerular tuft | Δ 0/8<br>▲ 0/8 | Δ 3/8<br>▲ 1/8 |
| Proteinaceous casts | Δ 0/8<br>▲ 0/8 | Δ 7/8<br>▲ 0/8 |
| Serum creatinine (mg/dl) | 0.58 ± 0.02* | 0.68 ± 0.02 |

In the above Table, *, Δ and ▲ mean the following, respectively.
*; $p < 0.01$
Atrophy of uniniferous tubule
Δ means the case where uniniferous tubule accompanied with epithelial cell with reduced staining properties, luminal constriction and winding basement membrane can be observed at the area of not less than 30% and less than 60% on the cut surface of kidney.
▲ means the case where the above changes are observed at the area of 60% or more on the cut surface of kidney.
Collapse or sclerosis of glomerular tuft
Δ means that collapse or sclerosis of glomerular tufts are observed in 30% or more and less than 60% of the total glomeruli on the cut surface.
▲ means the above changes are observed in 60% or more of the total glomeruli on the cut surface.
Proteinaceous cast
Δ means that the proteinaceous casts are scattered at cortical part.
▲ means that the proteinaceous casts are observed extensively at cortical part.

From Table 3, in the control group, histopathological changes such as atrophy of uniniferous tubule, collapse or sclerosis of glomerular tuft and proteinaceous casts which mean the presence of proteinuria, are remarkable. On the contrary, in the test compound administration group, it is apparent that such renal lesions are not recognized.

Also, in the control group, due to the fact that the serum creatinine is increased, it can be seen that rats of the control group are clinically suffered from renal failure. However, in the test compound administration group, such phenomena are not observed at all.

EXPERIMENTAL EXAMPLE 4

(Effect on Electrolyte Balance and Urine Volume)

Groups of 10 male SHR weighing 335 to 415 g were fasted overnight and then orally administered with 2.5 ml/100 g of physiological saline. One hour later, the rats were given (+)-cis-2-(4-methoxyphenyl)-3-acetoxy-5-[2-(dimethylamino)ethyl]-8-chloro-2,3-dihydro-1,5-benzothiazepin-4(5H)-one maleate dissolved in physiological saline at prescribed concentrations. Rats of the control group were given orally 2.5 ml/100 g of physiological saline instead of the test compound solution. Immediately afterwards, the animals were individually housed in a metabolic cage for 5 hr. The urine excreted during this period was collected and its volume was measured. The concentrations of electrolytes (sodium, potassium and chloride ions) in the urine were determined and the amounts excreted were calculated.

(Results)

The results are shown in Table 4.

TABLE 4

| Dose mg/kg | Urine volume ml/100 g/5 hr | Excretion of chloride μg Eq/100 g/5 hr | Excretion of sodium μg Eq/100 g/5 hr | Excretion of potassium μg Ec/100 g/5 hr | Sodium/Potassium ratio in urine |
|---|---|---|---|---|---|
| (Control) | 1.75 ± 0.69 | 298 ± 25 | 258 ± 22 | 65 ± 7 | 4.11 ± 0.37 |
| 3 | 2.14 ± 0.95 | 359 ± 47 | 327 ± 40 | 63 ± 9 | 5.36 ± 0.34 |
| 10 | 3.02 ± 0.15* | 527 ± 24* | 505 ± 24* | 68 ± 7 | 7.74 ± 0.56* |

*$P < 0.01$

As clearly shown in Table 4, the 8-chloro-benzothiazepine compound, which is an active ingredient of the present invention at the dose of 10 mg/kg increased the urine volume by 73% and the excretion of sodium and chloride ions by 96 and 77%, respectively, in comparison with those of the control group. However, the compound did not affect the excretion of potassium ion and therefore significantly increased the sodium/potassium ratio in the urine.

EXAMPLE 1

| (Tablet) | |
|---|---|
| (+)-Cis-8-chloro-benzothiazepine compound (maleate) | 45.0 g |
| Corn starch | 20.1 g |
| Lactose | 82.4 g |
| Polyvinyl pyrrolidone | 3.0 g |
| Crystalline cellulose | 38.0 g |
| Magnesium stearate | 1.5 g |
| Total | 190.0 g |

The (+)-cis-8-chlorobenzothiazepine compound (maleate), lactose and corn starch were mixed with an alcohol solution of polyvinyl pyrrolidone and granulated by kneading according to the wet granulation method, followed by drying to be formed into granules.

Subsequently, magnesium stearate and crystalline cellulose were added to the granules and the mixture is compressed by a tabletting machine to give tablets of 8 mm in diameter and 190 mg in weight.

EXAMPLE 2

(Injection)

Ten grams of (+)-cis-8-chlorobenzothiazepine compound (maleate) were dissolved in 2 liter of distilled water for injection. The solution was filtered through a membrane filter with a pore size of 0.22 μm, and was poured into ampoules under aseptic conditions each in 2 ml and sealed to give ampoules for injection.

EXAMPLE 3

| (Powders) | |
|---|---|
| (+)-Cis-8-chlorobenzothiazepine compound (maleate) | 10 g |
| Lactose | 90 g |
| Total | 100 g |

The above-mentioned ingredients were homogeneously mixed in a double conical mixer to give 10-fold trituration.

We claim:

1. A method for the treatment of renal failure in a warm-blooded animal which comprises administering to the animal in need of said treatment a therapeutically effective amount of 2-(4-methoxyphenyl)-3-acetoxy-5-[2-(dimethylamino)ethyl]-8-chloro-2,3-dihyro-1,5-benzothiazepin-4(5H)one or a pharmaceutically acceptable acid addition salt thereof.

2. The method according to claim 1, wherein the compound to be administered is (+)-cis-2-(4-methoxyphenyl)-3-acetoxy-5-[2-(dimethylamino)ethyl]-8-chloro-2,3-dihydro-1,5-benzothiazepin-4(5H)-one or a pharmaceutically acceptable acid addition salt thereof.

3. The method according to claim 2, wherein said pharmaceutically acceptable acid addition salt is one selected from the group consisting of hydrochloride, hydrobromide, hydroiodide, perchlorate, sulfate, phosphate, oxalate, maleate, fumarate, tartarate and methanesulfonate.

4. The method according to claim 3, wherein said pharmaceutically acceptable acid addition salt is maleate.

5. The method according to claim 4, wherein said therapeutically effective amount of the compound is 0.05 to 100 mg/kg/day.

6. A method for producing a diuretic effect on a warm-blooded animal which comprises administering to the animal in need of producing said effect a diuretic effective amount of 2-(4-methoxyphenyl)-3-acetoxy-5-[2-(dimethylamino)ethyl]-8-chloro-2,3-dihydro-1,5-benzothiazepin-4(5H)-one or a pharmaceutically acceptable acid addition salt thereof.

7. The method according to claim 6 wherein the compound to be administered is (+)-cis-2-(4-methoxyphenyl)-3-acetoxy-5-[2-(dimethyamino)ethyl]-8-chloro,2,3-dihydro-1,5-benzothiazepin-4(5H)-one or a pharmaceutically acceptable acid addition salt thereof.

* * * * *

UNITED STATES PATENT AND TRADEMARK OFFICE
CERTIFICATE OF CORRECTION

PATENT NO. : 4,822,789

DATED : April 18, 1989

INVENTOR(S) : Isao Yamaguchi, et al.

It is certified that error appears in the above-identified patent and that said Letters Patent is hereby corrected as shown below:

Column 3, Table 1, line 43: "1589 $\pm$ 123" should read as --1589 $\pm$ 105--

Signed and Sealed this

Fifth Day of June, 1990

Attest:

HARRY F. MANBECK, JR.

*Attesting Officer*      *Commissioner of Patents and Trademarks*